United States Patent
Aubert et al.

(10) Patent No.: US 8,101,667 B2
(45) Date of Patent: *Jan. 24, 2012

(54) PESTICIDAL TREATMENT OF STORED GOODS, ENCLOSURES, STRUCTURES AND WORKS OF ART, WITH SULPHUR COMPOUNDS

(75) Inventors: Thierry Aubert, Pau (FR); Jacques Auger, Veigne (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/689,259

(22) Filed: Mar. 21, 2007

(65) Prior Publication Data

US 2007/0191491 A1   Aug. 16, 2007

Related U.S. Application Data

(63) Continuation of application No. 10/525,477, filed as application No. PCT/FR03/02725 on Sep. 16, 2003, now abandoned.

(30) Foreign Application Priority Data

Sep. 19, 2002 (FR) ...................... 02 11605

(51) Int. Cl.
*A01N 25/00* (2006.01)
*A01N 25/02* (2006.01)
*A01N 41/12* (2006.01)

(52) U.S. Cl. ........................ 514/707; 424/405
(58) Field of Classification Search .................. 514/707; 424/405
See application file for complete search history.

(56) References Cited

U.S. PATENT DOCUMENTS

| 2,045,925 | A | * | 6/1936 | Remy | ............................ | 514/706 |
| 4,447,447 | A | * | 5/1984 | Hreschak et al. | ............. | 514/473 |
| 6,511,674 | B1 | * | 1/2003 | Arand et al. | .................. | 424/406 |

FOREIGN PATENT DOCUMENTS

WO   WO 02/50053   *   6/2002

OTHER PUBLICATIONS

Auger et al., "A Possible New Class of Natural Sulfur Pesticides for Fumigation", Ecologie (1994), 25(2), pp. 93-101.*
Dugravot et al. "Dimethyl Disulfide Exerts Insecticidal Neurotoxicity Through Mitochondrial Dysfunction and Activation of Insect KATP Channels," J. Neurophysiol. Jul. 2003, 90, pp. 259-270.*
Tandon, P.L. and Lal, B. "Comparative Efficacy of Synthetic Garlic Oil with some Modern Insecticides Against *Drosicha mangiferae* Green," Progressive Horticulture, 1980, vol. 12, pp. 61-66.*
Bando et al. "Insecticidal, acaricidal, and fungicidal activities of disulfide compounds," Noyaku Seisan Gijutsu, 1967, vol. 18, pp. 1-6.*
Ramakrishnan, V. et al. "Environmental Persistence of Diallyl Disulfide, an Insecticidal Principle of Garlic and Its Metabolism in Mosquito, *Culex Pipiens Quinquifasciatus* Say," Chemosphere, 1989, vol. 18, Nos. 7-8, pp. 1525-1529.*
Deb-Kirtaniya et al. "Extracts of garlic as possible source of insecticides," Indian J. Agric. Sci., Jun. 1980, 50(6), pp. 507-510.*

* cited by examiner

*Primary Examiner* — James H. Alstrum-Acevedo
(74) *Attorney, Agent, or Firm* — Steven D. Boyd

(57) ABSTRACT

The present invention is directed to the pesticidal treatment of stored foodstuffs, chambers, structures and works of art, using a volatile sulphur compound of general formula:

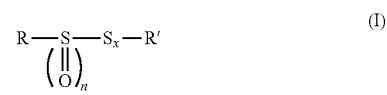

in which R represents an alkyl or alkenyl radical containing from 1 to 4 carbon atoms, n is equal to 0, 1 or 2, x is a number ranging from 0 to 4, and R' represents an alkyl or alkenyl radical containing from 1 to 4 carbon atoms or, only if n=x=0, a hydrogen atom. These sulphur compounds (in particular dimethyl disulphide) are applied by nebulization directly to the material to be treated.

2 Claims, 1 Drawing Sheet

PESTICIDAL TREATMENT OF STORED GOODS, ENCLOSURES, STRUCTURES AND WORKS OF ART, WITH SULPHUR COMPOUNDS

CROSS REFERENCE TO RELATED APPLICATIONS

This application is a continuation of application Ser. No. 10/525,477 filed Jul. 14, 2005.

FIELD OF THE INVENTION

The present invention relates to the field of the pesticidal treatment of stored foodstuffs, chambers and structures, and works of art, and its subject is more particularly a pesticidal treatment by nebulization using sulphur compounds.

BACKGROUND OF THE INVENTION

Currently, the pesticidal treatment of stored foodstuffs, chambers, structures and works of art is essentially carried out according to two techniques:
fumigation, using in particular methyl bromide (MB) and phosphine ($PH_3$) which act in the gaseous state on the respiratory chain of the target organisms,
so-called "contact" treatments using, for example, organophosphorus insecticides, in particular dichlorvos, which act in the condensed state directly on the target organisms.

Methyl bromide (MB) exhibits in the gaseous state excellent nematicidal, fungicidal, insecticidal and bactericidal properties. Unfortunately, this compound contributes to depletion of the ozone layer and, in accordance with the Montreal Accord (1992), by 2005 it should no longer be used in industrialized countries. Phosphine ($PH_3$) exhibits major disadvantages such as its toxicity, the duration of the treatments and the corrosion of equipment in which this compound is used (Pest Control (1999) Vol. 67(1), p. 46).

Moreover, organophosphorus compounds have an activity spectrum reduced to their insecticidal action and generate toxic residues. In addition, since they only act through contact directly with the target organisms, they cannot reach the so-called hidden forms of these organisms; accordingly, the eggs and larvae of the insects present inside the grains of wheat and maize are not killed by the insecticide. This type of treatment is markedly less effective.

There is therefore an urgent need to provide users with alternative solutions which are effective and which are as environmentally friendly as possible. Examples of fumigant products under development for these applications are known and are described in various articles, in particular in World Grain, February 2001, p. 28-30 and Crop Prot. (2000) 19 (8-10), p. 577-582); but the solutions envisaged also exhibit major disadvantages such as their high cost (methyl iodide), their low availability (carbon oxysulphide) or their toxicity (sulphuryl fluoride).

Another family of compounds, the sulphur-containing products derived from substances produced by certain plants, for example the Alliums, is also known for its pesticidal and repellent activity and has already been the subject of numerous publications (Ecologie (1994) 25(2), p 93-101, Ed. Tec. and Doc., Biopesticides d'origine végétale (2002) p 77-95, Insect Sci. Applic. (1989) 10(1), p. 49-54, Pestic. Sci. (1999), Vol. 55, p. 197-218). The use of these sulphur compounds as fumigants in the treatment of stored foodstuffs has never been generally accepted. Patent application FR-A-2 779 615 filed in 1997 discloses a particular technique for the application of such treatments: the circulation of gas in a loop in a sealed silo by means of a pump. Indeed, it is essential for a fumigant for the treatment of stored foodstuffs to diffuse the treatment rapidly in the gaseous form in the mass to be treated. However, it has been demonstrated by the applicant that these sulphur-containing products spontaneously diffuse too slowly in a mass of grains, causing large differences in the gas concentration inside this mass and therefore an inefficiency in the treatment. The solution proposed in the abovementioned patent application, consisting in carrying the active gas in a stream of air or of air enriched with $CO_2$, is an expensive technique which is not available on the majority of existing installations and which is difficult to apply because of the lack of leaktightness in the majority of installations for the storage of foodstuffs.

DETAILED DESCRIPTION OF THE INVENTION

Figure 1:
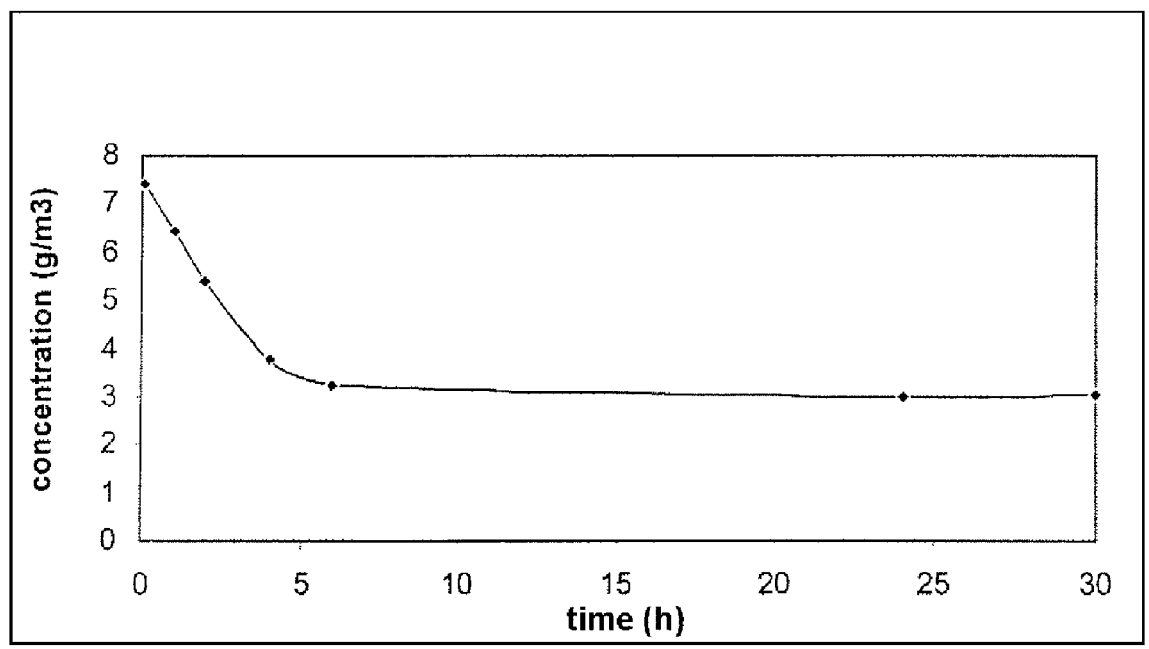
FIG. 1 is a graph of dimethyl disulphide concentration versus time in a treated chamber.

It has now been found that the sulphur compounds of general formula:

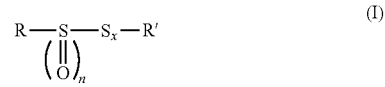

(I)

in which R represents an alkyl or alkenyl radical containing from 1 to 4 carbon atoms, n is equal to 0, 1 or 2, x is a number ranging from 0 to 4, and R' represents an alkyl or alkenyl radical containing from 1 to 4 carbon atoms or, only if n=x=0, a hydrogen atom, are particularly advantageous fumigants for the treatment of stored foodstuffs when they are applied by nebulization like contact insecticides. The subject of the present invention is therefore a pesticidal treatment of stored foodstuffs, characterized in that at least one volatile sulphur compound of formula (I) is applied by nebulization. The sulphur compounds of formula (I) are all sufficiently volatile to pass rapidly, under the usual temperature and pressure conditions, from the liquid state to the gaseous state in which they are active. The nebulization technique has the advantage of applying the sulphur compounds directly at the site where they have to act, which solves the problem of their too slow spontaneous diffusion in the mass to be treated. Furthermore, it can be used in installations with imperfect leaktightness and in existing equipment intended for the application of contact insecticides.

The sulphur compounds of formula (I) not only exhibit pesticidal properties towards insects, fungi, bacteria, viruses, nematodes, arachnids and rodents, but also repellent properties towards insects, arachnids and rodents.

They are therefore perfectly suitable for the pesticidal and/or repellent treatment of dry or moist stored foodstuffs, such as wheat, maize, rice, apples, dry fruits and dry processed products such as for example animal foods, chambers and structures such as silos, timber, wooden structures including those used for the culture of mushrooms, including quarantine treatments. The invention also relates to the compounds of formula (I) applied by nebulization for the pesticidal and/or repellent treatment of works of art and other valuable objects derived from plant or animal products, such as for example paintings, sculptures and fabrics.

As substitutes for methyl bromide, the compounds of formula (I) are all the more advantageous since they are already present in nature, being derived from the natural degradation of crucifers and alliums. In particular, the thiosulphinates, included in general formula (I), are products which are naturally emitted when alliums are ground and, in this regard, can be used in agricultural biology for the treatment of stored foodstuffs. Moreover, given that they do not contain halogen atoms which generate halogenated radicals responsible for the catalytic destruction of the stratospheric ozone, the compounds of formula (I) are without danger for the ozone layer.

As nonlimiting examples of radicals R and R', there may be mentioned methyl, propyl, allyl and 1-propenyl radicals. Among the compounds of formula (I), the compounds for which n=0 are preferred. Other preferred compounds are the disulphides (n=0, x=1) and more particularly dimethyl disulphide (DMDS).

The compounds of formula (I) can be used in the pure state or in various forms which, depending on the nature of the compound (I), can be an aqueous emulsion, a microemulsion, a microencapsulated product, a solution in water or in an organic solvent. All these formulations can be made according to methods well known to a person skilled in the art.

The organic solvents which may be used to dissolve the compounds of formula (I) according to the invention are hydrocarbons, alcohols, ethers, ketones, esters, halogenated solvents, mineral oils, natural oils and their derivatives, and aprotic polar solvents such as dimethylformamide, dimethyl sulphoxide or N-methylpyrrolidone. Biodegradable solvents, more particularly methyl esters of rapeseed and soybean oils, are particularly suitable.

The compounds of formula (I) are applied, in the forms described above according to the method known to a person skilled in the art for contact insecticides, by nebulization of the pure or formulated product directly onto the material to be treated, in an atmosphere of pure air or of air enriched with $CO_2$.

The doses of compounds (I) to be used in order to obtain the desired effect should meet an objective in terms of CT, that is to say the product of the concentration C of active substance in the air and of the time T during which the product is allowed to act. The product CT indicates the cumulative dose of the active compound to which the pathogenic organisms are subjected during the treatment. The objective is to reach a value of the product CT, called lethal CT, corresponding to the complete destruction of the target organisms. For an optimum treatment, the value of the lethal product CT should be reached as rapidly as possible and in the most homogeneous manner possible in the mass or on the material to be treated; this is obtained using the method of application of the compound by nebulization.

The lethal CT values are generally between 20 and 200 $ghm^{-3}$ and depend on the nature of the compound (I), the level of infestation, the nature of the target organism, the type of material to be treated, and the ventilation of the chambers.

Once the lethal effect has been obtained, the product (I) is removed by ventilation and therefore generates no residue on the material to be treated.

The following examples illustrate the invention without limiting it.

Example 1 (Comparative)

In this example, dimethyl disulphide (DMDS) is used as compound of formula (I) and its spontaneous diffusion in a silo of wheat grains is studied.
Materials and Methods:
Temperature: 20° C.
Dimensions of the silo:
total height: 80 cm
diameter: 46 cm
total volume: 130 l
filling level: 80%, that is 79 kg of wheat
grain height: 72 cm
Pure DMDS is deposited at a concentration of 30 $gm^{-3}$ at the surface of the grains using a syringe.

There are then measured by gas chromatography as a function of time (in hours) the concentrations of DMDS in gaseous form at the surface of the silo of wheat grains where DMDS is introduced (point A: 0 cm), and at 36 cm below the level of the grains in the silo (point B: −36 cm) and at the lower end of the silo (point C: −72 cm).

The products CT of the concentrations C of DMDS by the time of measurement T are determined at the various points of measurement over a period of 3 days. The CT values in $ghm^{-3}$ indicated in Table 1 are thus observed.

TABLE 1

| Time (days) | CT | | |
| --- | --- | --- | --- |
| | A | B | C |
| 1 | 542 | 46 | 4 |
| 2 | 630 | 80 | 14 |
| 3 | 821 | 180 | 62 |

The products CT for DMDS are not homogeneous in the entire thickness of the silo, even after a long residence time. The conditions for the application of DMDS in this example do not make it possible to obtain a sufficiently rapid spontaneous diffusion of the fumigant.

Example 2

This example, which does not use application by nebulization, makes it possible to obtain a concentration gradient over the height of the chamber and to thus determine the values of the lethal product CT in a silo of wheat grains infested with two pathogenic organisms usually encountered as principal pests of stored foodstuffs. These two organisms are *Sitophilus granarius* and *Sitophilus orizae*.
Materials and Methods
Temperature: 20° C.
Dimensions of the silo:
total height: 40 cm
total volume: 3.3 l
filling level: 75%, that is a grain height of about 33 cm.
99 mg of pure DMDS are deposited at the surface of the grains using a syringe. The samples collected consist of bundles of 50 g of wheat containing all the stages of development of the pathogenic organisms. After degassing by aeration of the silo at the times T, the bundles of wheat are screened and the adults are counted immediately after screening (D+0) and after 14 days (D+14). The wheat containing the other stages of development is then examined for 5 weeks.

The products CT of the concentrations C of DMDS by the times of measurement T are determined and the efficacy of the treatment in relation to the 2 pathogenic organisms studied for all the stages of development is monitored as a function of these products CT. The results are expressed:
  as a percentage of the adult mortality at the times (D+0) and (D+14).
  as a percentage of net emergence reduction (% NER) relative to an untreated control batch for the different stages of development of these organisms (that is to say eggs and 2nd generation, eggs and 1st stage larvae, 1st and 2nd stage larvae, 2nd and 3rd stage larvae, 3rd and 4th stage larvae, 4th stage larvae and nymphs), which corresponds to the following formula:

% NER=(number of insects which emerged live from the control batch−number of insects which emerged live from the treated batch)/(number of insects which emerged live from the control batch).

A—Case of *Sitophilus Granarius*
The results are assembled in Table 2.

TABLE 2

% NER for the various stages of the batch treated with DMDS

| | % adult mortality | | Eggs and 2nd generation | Eggs and Ist stage larvae | Ist and IInd stage larvae | IInd and IIIrd stage larvae | IIIrd and IVth stage larvae | IVth stage larvae and nymphs | Total No. of insects emerged | % NER |
|---|---|---|---|---|---|---|---|---|---|---|
| CT | D+0 | D+14 | | | | | | | | |
| 5.8 | 0 | 8 | 13 | 41 | 20 | 13 | 3 | 21 | 202 | 25 |
| 6.1 | 3 | 9 | 33 | 5 | 80 | 16 | 19 | 54 | 208 | 23 |
| 15.0 | 64 | 93 | 25 | 54 | 88 | 71 | 26 | 75 | 126 | 54 |
| 26.9 | 92 | 92 | 20 | 79 | 88 | 94 | 65 | 92 | 75 | 72 |
| 50.5 | 100 | 100 | 93 | 100 | 100 | 100 | 97 | 100 | 4 | 99 |
| 88.4 | 100 | 100 | 95 | 100 | 100 | 100 | 100 | 100 | 2 | 99 |
| 160.4 | 100 | 100 | 100 | 100 | 100 | 100 | 100 | 100 | 0 | 100 |
| Number of insects which emerged live from the untreated control batch | | | | | | | | | | |
| | | | 40 | 120 | 25 | 31 | 31 | 24 | 271 | |

Table 2 shows that a product CT of 160 gh.m$^{-3}$ results in a mortality of 100% for all the stages of development of *Sitophilus granarius* and that from CT values greater than 50 gh.m$^{-3}$, 100% mortality is obtained for the majority of the stages. The pesticidal efficacy of DMDS against the pathogenic organism *Sitophilus granarius* is evaluated in terms of the product CT at about 100 ghm$^{-3}$ (useful CT).

B—Case of *Sitophilus Orizae*

Under the same trial conditions, this time on organisms of the *Sitophilus orizae* type, similar results are obtained. The pesticidal efficacy of DMDS against the pathogenic organism *Sitophilus orizae* is evaluated in terms of the product CT at about 100 ghm$^{-3}$ (useful CT).

Example 3

In this example, use is made of DMDS formulated as a 30% solution in a methyl ester of rapeseed oil (Radia®7961 provided by the OLEON company). Its efficacy is studied in a silo of wheat grains by monitoring its absorption onto the grains as a function of time after its application by nebulization.

Materials and Methods
Temperature: 20° C.
Chamber:
total volume: 31
total height: 28 cm
filling with 1 kg of wheat grains, that is a height of 15 cm
There are introduced 90 mg of pure DMDS as a solution in 210 mg of Radia®7961 by 2 successive sprayings by means of a nebulizer. The chamber is immediately mechanically stirred so as to rapidly homogenize the gas concentration in the treated mass.

The DMDS concentrations in the atmosphere in the chamber are monitored for 5 days by SPME-GC-MS analysis. FIG. 1 illustrates the concentration of DMDS in the atmosphere of the chamber as a function of time for the first 30 hours. It is observed that the concentration of DMDS in the atmosphere of the chamber decreases regularly during the first 5 hours to reach the value of 3 gm$^{-3}$ which then remains constant during the 5 days. The useful product CT of 100 ghm$^{-3}$ corresponding to an optimum efficacy of DMDS is reached after 30 hours of treatment under the application conditions of the invention.

The invention claimed is:

1. A process of pesticidal treatment of stored foodstuffs and silos comprising applying to foodstuffs dimethyl disulphide (DMDS) by nebulization in the form of a solution in a biodegradable solvent selected from the group consisting of methyl esters of rapeseed oils, methyl esters of soybean oils and mixtures thereof.

2. The process according to claim 1, wherein the product CT of the concentration of dimethyl disulphide (DMDS) applied (C) and of the time (T) for which the dimethyl disulphide (DMDS0 is allowed to act, in order to obtain complete destruction of the target organisms, is between 20 and 200 ghm$^{-3}$.

* * * * *